United States Patent [19]

Prost

[11] Patent Number: 5,021,417

[45] Date of Patent: Jun. 4, 1991

[54] USE OF A FOLINIC ACID SUBSTANCE AS A PLATELET AGGREGATION INHIBITOR

[75] Inventor: Michel Prost, Couternon, France

[73] Assignee: Spiral Recherche et Developpement, Couternon, France

[21] Appl. No.: 465,090

[22] PCT Filed: May 29, 1989

[86] PCT No.: PCT/FR89/00257

§ 371 Date: Jan. 18, 1990

§ 102(e) Date: Jan. 18, 1990

[87] PCT Pub. No.: WO89/11280

PCT Pub. Date: Nov. 30, 1989

[30] Foreign Application Priority Data

May 27, 1988 [FR] France .................. 88 07075

[51] Int. Cl.⁵ .................. A61K 31/50; A61K 31/495
[52] U.S. Cl. .................. 514/249
[58] Field of Search .................. 514/249

[56] References Cited

PUBLICATIONS

Stadtler et al.—Onkologie, vol. 7, No. 4, Aug. 1984, 238-242.
Shaw—Scand. J. Haemat., (1973), vol. 10, pp. 24-27.
Cooper et al.—Brit. J. of Haematology, 1976, 32, pp. 387-394.
Nixon—Clinical and Experimental Pharmacology & Physiology, (1979), Suppl. 5, pp. 35-41.

*Primary Examiner*—Stanley J. Friedman
*Attorney, Agent, or Firm*—Fleit, Jacobson, Cohn, Price, Holman & Stern

[57] ABSTRACT

The present invention relates to a novel use in therapy of a folinic acid substance or substance analogous to folinic acid, said use being characterized in that a substance selected from the group consisting of 5,6,7,8-tetrahydrofolic acid, its derivatives and mixtures thereof is used in order to obtain a platelet aggregation inhibiting drug intended for a therapeutic indication in cases where it is appropriate to inhibit or reduce blood platelet aggregation.

4 Claims, No Drawings

USE OF A FOLINIC ACID SUBSTANCE AS A PLATELET AGGREGATION INHIBITOR

FIELD OF THE INVENTION

The present invention relates to the use of folinic acid compounds belonging to the family of the folinic acid derivatives and analogues comprising in their molecule the 5,6,7,8-tetrahydrofolic acid radical of the formula

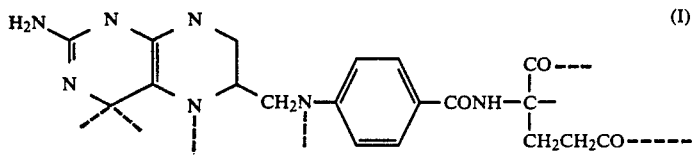

(I)

in which the dashes --- denote a bond with a hydrogen atom in the 4, 5 and/or 10 positions, a bond with an OH group as a substituent of at least one of the two carbonyl groups of the glutamyl residue, or any other suitable group in the 4, 5 and/or 10 positions or as a substituent of at least one of the two carbonyl groups of the glutamyl residue.

PRIOR ART

It is known that folic acid, which corresponds to the systematic nomenclature of N-[4-[[(2-amino-1,4-dihydro-4-oxo-6-pteridinyl)methyl]amino]benzoyl]-L-glutamic acid, and its alkali metal and alkaline earth metal salts act in the organism as vitamin substances [see Merck Index, 10th edition (1983), pages 602–603].

It is known that folinic acid, which corresponds to the systematic nomenclature of N-[4-[[(2-amino-5-formyl-1,4,5,6,7,8-hexahydro-4-oxo-6-pteridinyl)methyl]amino]benzoyl]-L-glutamic acid and to the abbreviated nomenclature of 5-formyl-5,6,7,8-tetrahydrofolic acid, and its salts act in the organism as antidotes to folic acid antagonists [see Merck Index, 10th edition (1983), page 603].

It is known that methotrexate, which corresponds to the systematic nomenclature of N-[4-[[(2,4-diamino-6-pteridinyl)methyl]methylamino]benzoyl]-L-glutamic acid and to the abbreviated nomenclature of 4-amino-$N^{10}$-methylfolic acid, is a folic acid antagonist and acts in the organism as an antineoplastic and antimetabolite. More precisely, it is known that methotrexate blocks (i) the conversion of folic acid to folinic acid and (ii) the synthesis of DNA, on the one hand, and acts as a substance which induces blood platelet aggregation, on the other. It is also known that methotrexate has caused accidents when administered to cancer patients [see Merck Index, 10th edition (1983), pages 859–860].

It is known in particular that the article by M. T. SHAW, Scand. J. Haemat., 10, pages 24–27, 1973, relating to pregnant women presenting trophoblastic tumours, refers to a decrease in the number of platelets after the administration of a treatment comprising a combination of methotrexate (administered intravenously or intramuscularly) and folinic acid (administered intramuscularly). The protocol followed and the results provided by said article do not suggest that folinic acid has blood platelet aggregation inhibiting properties, especially since said acid was not used by itself.

It is known that methopterin, which corresponds to the systematic nomenclature of N-[4-[[(2-amino-4-hydroxy-6-pteridinyl)methyl]methylamino]benzoyl]-L-glutamic acid and is also called $N^{10}$-methylfolic acid, is a folic acid derivative which has been described in U.S. Pat. No. 2,563,707 [see also Merck Index, 10th edition (1983), page 859].

Finally, it is known that 5-methyl-5,6,7,8-tetrahydrofolic acid, which corresponds to the systematic nomenclature of N-[4-[[(2-amino-1,4,5,6,7,8-hexahydro-5-methyl-4-oxo-6-pteridinyl)methyl]amino]benzoyl]-L-glutamic acid and has the abbreviated nomenclature of 5-N-Me-THF, on the one hand, and folinic acid, on the other, have been proposed in therapy as antistress drugs.

SUBJECT OF THE INVENTION

According to the invention, a novel use of a folinic acid substance or substance analogous to folinic acid as a platelet aggregation inhibitor is proposed.

More precisely, a novel use in therapy of a folinic acid substance or substance analogous to folinic acid is recommended according to the invention, said use being characterized in that a substance selected from the group consisting of 5,6,7,8-tetrahydrofolic acid, its derivatives and mixtures thereof is used in order to obtain a platelet aggregation inhibiting drug intended for a therapeutic indication in cases where it is appropriate to inhibit or reduce blood platelet aggregation.

This novel use in therapy according to the invention is neither described nor suggested by the teaching of the prior art summarized above.

In other words, the platelet aggregation inhibiting active ingredient according to the invention comprises in its molecule the 5,6,7,8-tetrahydrofolyl radical of the formula

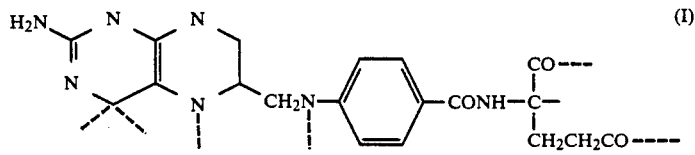

(I)

in which the dashes --- denote a bond with a hydrogen atom in the 4, 5 and/or 10 positions, a bond with an OH group as a substituent of at least one of the two carbonyl groups of the glutamyl residue, or any other suitable group in the 4, 5 and/or 10 positions or as a substituent of at least one of the two carbonyl groups of the glutamyl residue.

DETAILED DESCRIPTION OF THE INVENTION

The invention therefore relates to a novel use of 5,6,7,8-tetrahydrofolic acid and its derivatives as platelet aggregation inhibitors.

Said derivatives include especially those which have in their molecule (a) a hydroxyl, amino or oxo group in the 4 position, (b) a $C_1$–$C_4$ alkyl group (especially methyl group) or an acyl group (especially formyl or acetyl group) in the 5 position, (c) a $C_1$–$C_4$ alkyl group (especially methyl group) in the 10 position, and/or (d) one of the COOH groups of the glutamic acid residue or both groups of said glutamic acid residue converted to ester or amide groups.

From a practical point of view, the platelet aggregation inhibitor is selected from the group consisting of (i) the 5,6,7,8-tetrahydrofolic acids and their salts of the formula

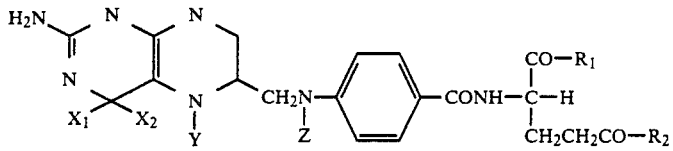

in which $X_1$ and $X_2$, which are identical or different, each represent H, OH or $NH_2$, it being possible for $X_1$ and $X_2$, taken together, to form an oxo group with the carbon atom to which they are bonded, Y represents H, CHO, $COCH_3$ or a $C_1$–$C_4$ alkyl group, the preferred alkyl group being $CH_3$, Z represents H or a $C_1$–$C_4$ alkyl group, the preferred alkyl group being $CH_3$, and $R_1$ and $R_2$, which are identical or different, each represent OH or a basic radical, especially $NH_4+$ or $1/m$ $M^{+m}$, in which M is a metal atom and m its valency;

(ii) the esters in which at least one of the radicals $R_1$ and $R_2$ represents an alkoxy, aralkoxy, aryloxy or heteroaryloxy group;

(iii) the amides in which at least one of the radicals $R_1$ and $R_2$ represents a substituted or unsubstituted amino group; and (iv) mixtures thereof.

According to the best way of carrying out the invention, the platelet aggregation inhibiting active ingredient is selected from the group consisting of (a) folinic acid, which corresponds to the systematic nomenclature of N-[4-[[(2-amino-5-formyl-1,4,5,6,7,8-hexahydro-4-oxo-6-pteridinyl)methyl]amino]benzoyl]-L-glutamic acid, (b) 4-amino-$N^{10}$-methyl-5,6,7,8-tetrahydrofolic acid, which corresponds to the systematic nomenclature of N-[4-[[(2,4-diamino-1,4,5,6,7,8-hexahydro-6-pteridinyl)-methyl]-methylamino]benzoyl]-L-glutamic acid, (c) $N^{10}$-methyl-5,6,7,8-tetrahydrofolic acid, which corresponds to the systematic nomenclature of N-[4-[[(2-amino-1,4,5,6,7,8-hexahydro-4-hydroxy-6-pteridinyl)methyl]methylamino]benzoyl]-L-glutamic acid, (d) 5-formyl-$N^{10}$-methyl-5,6,7,8-tetrahydrofolic acid, which corresponds to the systematic nomenclature of N-[4-[[(2-amino-5-formyl-1,4,5,6,7,8-hexahydro-4-hydroxy-6-pteridinyl)methyl]methylamino]benzoyl]-L-glutamic acid, (e) 5-methyl-5,6,7,8,-tetrahydrofolic acid, which corresponds to the systematic nomenclature of N-[4-[[(2-amino-1,4,5,6,7,8-hexahydro-5-methyl-4-oxo-6-pteridinyl)-methyl)amino]benzoyl]-L-glutamic acid, and (f) their alkali metal and alkaline earth metal salts.

The products according to the invention which are of greatest value with regard to their platelet aggregation inhibiting properties are, in particular, 5-methyl-5,6,7,8-tetrahydrofolic acid and its alkali metal and alkaline earth metal salts such as the sodium, potassium and calcium salts.

In practice, it is assumed that the efficacy of 5-methyl-5,6,7,8-tetrahydrofolic acid is related to the hydrophobic character of the 5-methyl group, which facilitates or improves the bioavailability to the cells. Although the applicant is not bound by this theory, it is preferred, according to the invention, to use the compounds of formula II which are hydrophobic, such as said 5-methyl-5,6,7,8-tetrahydrofolic acid, and which generally display a greater platelet aggregation inhibiting activity than folinic acid with regard to their ability to penetrate the cells.

It is recommended, according to the invention, to use a therapeutic composition which contains, in association with a physiologically acceptable excipient, a pharmaceutically effective amount of a platelet aggregation inhibitor belonging to the family of the 5,6,7,8-tetrahydrofolic acids and their derivatives.

Such a composition is useful in human therapy and in veterinary therapy for warm-blooded animals. More precisely, it is suitable for the treatment of mammals and, in particular, man.

The platelet aggregation inhibiting active principles according to the invention can be prepared according to a method known per se by the application of conventional reaction mechanisms.

Further advantages and characteristics of the invention will be understood more clearly from the following description of results of pharmacological tests using the preferred aggregation inhibitor according to the invention, namely 5-methyl-5,6,7,8-tetrahydrofolic acid, on the one hand in the presence of a substance known for its aggregating properties, namely methotrexate, and on the other hand in the presence of a contraceptive, namely ethynyloestradiol.

FIRST SERIES OF EXPERIMENTS

In a first series of experiments, the pharmacological tests were performed on adult male rats, the rats being divided into groups of ten animals each, namely:

a control group C receiving only the vehicle, consisting of dimethylsulfoxide and NaCl at 9 g/l, by subcutaneous administration;

a treated group M receiving methotrexate (0.5 mg/kg) in the above-mentioned vehicle by subcutaneous administration; and a treated group N receiving methotrexate (0.5 mg/kg) in the above-mentioned vehicle by subcutaneous administration, and 5-methyl-5,6,7,8-tetrahydrofolic acid (0.5 mg/kg), also by subcutaneous administration.

The injections are given at a fixed time for 3 days. On the fourth day, blood samples are taken from the fasted animals and the blood platelets are isolated by the conventional techniques and resuspended in a buffer. The aggregating activity of these platelets is tested during stimulation with small doses of thrombin. The results are expressed (in mm) by the amplitude of the aggregation curve obtained. These results are collated in Table I below.

TABLE I

| GROUP | PLATELET AGGREGATION (mm) | (%) |
|---|---|---|
| C | 20.4 ± 6.5 | 100 |
| M | 171.5 ± 9.7 | 855 |
| N | 8.7 ± 1.8 | 44 |

SECOND SERIES OF EXPERIMENTS

In a second series of experiments, the following were administered to female rats weighing 200 to 300 g: on the one hand methotrexate by subcutaneous administration or a contraceptive by intubation, and on the other hand folinic acid or 5-methyl-5,6,7,8-tetrahydrofolic acid by subcutaneous administration or by gavage.

(a) Groups of female rats receive methotrexate (0.5 mg/kg) by subcutaneous administration for three days. Other groups are treated for the same period with folinic acid or 5-methyl-5,6,7,8-tetrahydrofolic acid (0.5 mg/kg) by subcutaneous administration or oral administration (by gavage), the control group receiving the excipient for the methotrexate, the excipient for the folinic acid and the excipient for the 5-methyl-5,6,7,8-tetrahydrofolic acid. The analyses are performed on the fasted animals on the day following the last day of treatment. The blood samples are taken via the jugular vein, after light anaesthesia, for preparation of the plasmas, erythrocytes and blood platelets.

Aggregation on platelet rich plasma (PRP)

Aggregation is induced with thrombin and ADP. The methotrexate is administered between 9 and 10 o' clock on days $D_1$, $D_2$ and $D_3$; the folinic acid and the 5-methyl-5,6,7,8-tetrahydrofolic acid are administered between 9 and 10 o' clock on days $D_1$, $D_2$ and $D_3$. The samples are taken from the fasted animals on day $D_4$.

The results obtained are shown in Table II below.

Aggregation of isolated platelets

Aggregation is induced with thrombin and ADP. The methotrexate is administered between 9 and 10 o'clock on days $D_1$, $D_2$ and $D_3$; the folinic acid and the 5-methyl-5,6,7,8-tetrahydrofolic acid are administered between 9 and 10 o'clock on days $D_1$, $D_2$ and $D_3$. The samples are taken from the fasted animals on day $D_4$.

The results obtained are shown in Table III below.

(b) Groups of female rats receive a contraceptive, namely 5 micrograms of ethynyloestradiol and 250 micrograms of lynoestrenol by oral administration (intubation) for four days. Other groups are treated for the same period with folinic acid or 5-methyl-5,6,7,8-tetrahydrofolic acid (0.5 mg/kg) by subcutaneous administration or oral administration (by gavage), the control group receiving the excipient for the contraceptive, the excipient for the folinic acid and the excipient for the 5-methyl-5,6,7,8-tetrahydrofolic acid. The analyses are performed on the fasted animals on the day following the last day of treatment. The blood samples are taken via the jugular vein, after light anaesthesia, for preparation of the plasmas, erythrocytes and blood platelets.

Aggregation on platelet rich plasma (PRP)

Aggregation is induced with thrombin and ADP. The contraceptive is administered between 9 and 10 o'clock on days $D_1$, $D_2$, $D_3$ and $D_4$; the folinic acid and the 5-methyl-5,6,7,8-tetrahydrofolic acid are administered between 9 and 10 o'clock on days $D_1$, $D_2$, $D_3$ and $D_4$. The samples are taken from the fasted animals on day $D_5$.

The results obtained are shown in Table IV below.

Aggregation of isolated platelets

Aggregation is induced with thrombin and ADP. The contraceptive is administered between 9 and 10 o'clock on days $D_1$, $D_2$, $D_3$ and $D_4$; the folinic acid and the 5-methyl-5,6,7,8-tetrahydrofolic acid are administered between 9 and 10 o'clock on days $D_1$, $D_2$, $D_3$ and $D_4$. The samples are taken from the fasted animals on day $D_5$.

The results obtained are shown in Table V below.

The results relating to the platelet aggregation measurements are all expressed in millimetres on the aggregation curves according to the mean/standard deviation system (n=3 to 5). They show that the preferred product according to the invention, namely 5-methyl-5,6,7,8-tetrahydrofolic acid, referred to here as 5-N-ME-THF, manifests its aggregation inhibiting effects in particular when the subject's platelet aggregation is too high.

TABLE II

| Product | Platelet aggregation (mm) | |
|---|---|---|
| | Thrombin | ADP |
| Control | 55 ± 6(d) | 132 ± 14(d) |
| Folinic acid | 74 ± 11 | 136 ± 27 |
| 5-N-Me-THF | 65 ± 10 | 128 ± 9 |
| Methotrexate | 135 ± 9(d) | 202 ± 11(d) |
| Methotrexate + folinic acid | 120 ± 11(a) | 141 ± 9(c) |
| Methotrexate + 5-N-Me-THF | 76 ± 14(b) | 115 ± 8(d) |

Notes
5-N-Me-THF: 5-methyl-5,6,7,8-tetrahydrofolic acid;
(a) $p < 0.05$, statistically significant according to the Student test;
(b) $p < 0.025$, statistically significant according to the Student test;
(c) $p < 0.005$, statistically significant according to the Student test;
(d) $p < 0.001$, statistically significant according to the Student test.

TABLE III

| Product | Platelet aggregation (mm) | |
|---|---|---|
| | Thrombin | ADP |
| Control | 118 ± 8(c) | 130 ± 11(d) |
| Folinic acid | 120 ± 11 | 126 ± 13 |
| 5-N-Me-THF | 82 ± 7(b) | 101 ± 8(a) |
| Methotrexate | 161 ± 6(d) | 231 ± 7(d) |
| Methotrexate + folinic acid | 136 ± 17 | 202 ± 14 |
| Methotrexate + 5-N-Me-THF | 63 ± 6(d) | 96 ± 6(d) |

Notes
5-N-Me-THF: 5-methyl-5,6,7,8-tetrahydrofolic acid;
(a) $p < 0.05$, statistically significant according to the Student test;
(b) $p < 0.025$, statistically significant according to the Student test;
(c) $p < 0.005$, statistically significant according to the Student test;
(d) $p < 0.001$, statistically significant according to the Student test.

TABLE IV

| Product | Platelet aggregation (mm) Thrombin |
|---|---|
| Control | 103 ± 7 |
| Contraceptive | 128 ± 17 |
| Contraceptive + folinic acid | 113 ± 9 |
| Contraceptive + 5-N-Me-THF | 99 ± 11 |

Notes
5-N-Me-THF: 5-methyl-5,6,7,8-tetrahydrofolic acid;
C: ethynyloestradiol and lynoestrenol.

TABLE V

| Product | Platelet aggregation (mm) Thrombin | Platelet aggregation (mm) ADP |
|---|---|---|
| Control | 132 ± 9 | 171 ± 8(d) |
| Folinic acid | 140 ± 18 | 124 ± 19(a) |
| 5-N-Me-THF | 160 ± 31 | 112 ± 16(b) |
| Contraceptive | 172 ± 24(c) | 328 ± 22(d) |
| Contraceptive + folinic acid | 161 ± 18 | 238 ± 7(c) |
| Contraceptive + 5-N-Me-THF | 61 ± 8(c) | 144 ± 12(d) |

Notes
5-N-Me-THF: 5-methyl-5,6,7,8-tetrahydrofolic acid;
C: ethynyloestradiol + lynoestrenol;
(a) $p < 0.05$, statistically significant according to the Student test;
(b) $p < 0.025$, statistically significant according to the Student test;
(c) $p < 0.005$, statistically significant according to the Student test;
(d) $p < 0.001$, statistically significant according to the Student test.

I claim:

1. A method of treatment for reducing blood platelet aggregation in a mammal, comprising the step of administering to the mammal a therapeutically effective amount of a blood platelet aggregation inhibiting substance selected from the group consisting
    (i) N-[4-[[(2-amino-1,4,5,6,7,8-hexahydro-5-methyl-4-oxo-6-pteridinyl)methyl]amino]benzoyl]-L-glutamic acid,
    (ii) alkali metal and alkaline earth metal salts thereof and
    (iii) mixtures thereof.

2. A method according to claim 1, for reducing blood platelet aggregation in a human, comprising the step of administering to a patient a therapeutically effective amount of a blood platelet aggregation inhibiting substance selected from the group consisting of:
    (i) N-[4-[[(2-amino-1,4,5,6,7,8-hexahydro-5-methyl-4-oxo-6-pteridinyl)methyl]amino]benzoyl]-L-glutamic acid,
    (ii) alkali metal and alkaline earth metal salts thereof and
    (iii) mixtures thereof.

3. A method of claim 1, wherein the metal salts are selected from the group consisting of sodium, potassium and calcium salts.

4. A method of claim 2, wherein the metal salts are selected from the group consisting of sodium, potassium and calcium salts.

* * * * *